United States Patent [19]

Morrison et al.

[11] 4,333,344

[45] Jun. 8, 1982

[54] SYSTEM AND METHOD FOR TESTING THE REACTION OF RARE EARTH IONS

[75] Inventors: Clyde A. Morrison, Wheaton; Joseph P. Sattler, Silver Spring, both of Md.

[73] Assignee: The United States of America as represented by the Secretary of the Army, Washington, D.C.

[21] Appl. No.: 200,832

[22] Filed: Oct. 28, 1980

[51] Int. Cl.³ .................................. G01N 29/00
[52] U.S. Cl. ........................ 73/584; 73/601; 330/5.5
[58] Field of Search .......... 73/601, 584, 587, 596, 73/599, 66 L; 330/5.5

[56] References Cited

U.S. PATENT DOCUMENTS 3,583,212  6/1971  Nanney et al. .................. 73/584

Primary Examiner—Anthony V. Ciarlante
Attorney, Agent, or Firm—Nathan Edelberg; Robert P. Gibson; Saul Elbaum

[57] ABSTRACT

A crystalline bar is doped with a rare earth. The bar is transparent to radiation, such as from a laser, at a light wavelength which excites the rare earth ions in the bar and the light is modulated at the frequency at which the bar mechanically resonates.

The excited ion decay radiatively by light or non-radiatively by phonons. As the phonons decay, they excite the bar to resonate mechanically. The mechanical resonance may be coupled by a piezoelectric material and measured to give information respecting the phonon activity of the excited rare earth ions.

9 Claims, 4 Drawing Figures

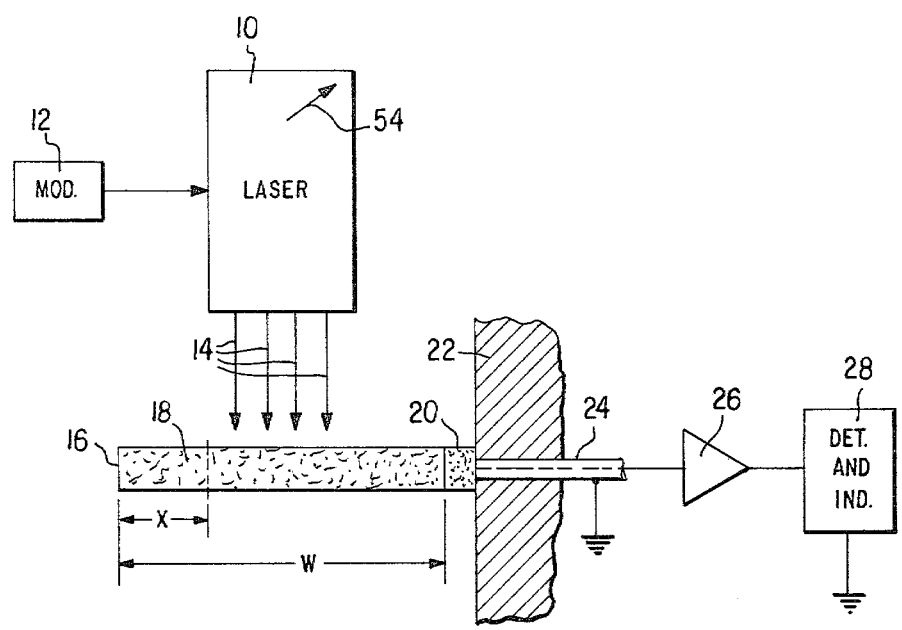
FIG. 1
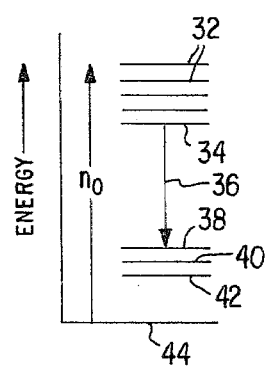
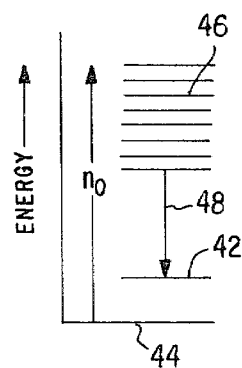
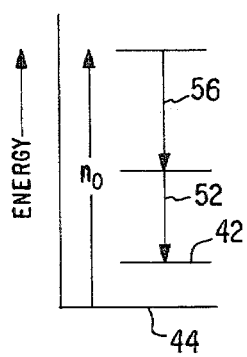
FIG. 2a    FIG. 2b    FIG. 2c

SYSTEM AND METHOD FOR TESTING THE REACTION OF RARE EARTH IONS

RIGHTS OF THE GOVERNMENT

The invention described herein may be manufactured, used and licensed by or for the U.S. Government for governmental purposes without the payment to me of any royalty thereon.

BACKGROUND OF THE INVENTION

The present invention is related to test systems and methods, and more particularly to a system and method for testing the reaction of rare earth ions in which a transparent crystalline solid is doped to respond to radiative light energy with which the ions are excited. It is known that the reactions of such excited ions is to decay from the excited state. The decay may be radiative, in which case the reaction is the radiation of light, or the reaction may be nonradiative, in which case the reaction is in the nature of phonons. The study of the radiative reactions is not too difficult since the light output may be studied and its frequency ascertained. Nevertheless, the study of the phonon output, which is in the nature of a vibratory elastic energy is difficult to study because it may not be directly observed.

SUMMARY OF THE INVENTION

According to the invention, a transparent bar doped with the rare earth ions to be studied is given dimensions to have a selected frequency of mechanical resonance. The bar is exposed to light radiation which is modulated at the desired frequency. The bar is coupled piezoelectrically to an output which thus affords an indication of the mechanical resonance resulting from the exposure to the light.

Phonons that result from the exposure excite the bar to resonate mechanically. By the nature and extent or amplitude of the mechanical resonance, the nature of the phonon reaction of the rare earth ions to the light may be studied and tested.

DESCRIPTION OF THE DRAWINGS

FIG. 1 is a schematic diagram illustrating an embodiment of the invention; and

FIGS. 2a, 2b and 2c are energy diagrams useful in explaining the reaction of the rare earth ions to light energy.

DETAILED DESCRIPTION OF THE PREFERRED EMBODIMENT

Referring to FIG. 1, a laser 10 is controlled by modulator 12 to provide a modulated light output indicated by the arrows 14. The light output 14 falls upon a suitable transparent, crystalline rod 16, for example of LiYF$_4$, doped with any of the rare earths as indicated by the speckling 18. The rod or bar 16 is mounted by means of a piezoelectric crystal 20 to a suitable mounting 22 and provides an electrical output which is coupled through a coaxial cable 24 to an amplifier 26. The amplifier 26 has an output applied to a detector and indicator 28. The coaxial cable output conductor, the amplifier 26, the detector and indicator 28 have a suitable common ground connection which is applied also to the crystal mounting of crystal 20 in a known fashion.

A laser has been selected for the light generator which is amplitude modulated because the light from the laser is substantially monochromatic. If this incident light is at a wavelength such that the rare earth ions or the doping by the rare earth absorbs the light, then the amount of the absorption will be also modulated at the modulating frequency, for example, F$_0$. The absorption is then converted into phonons insofar as the decay is nonradiative. Referring to FIGS. 2a, 2b and 2c, at least three possibilities suggest themselves. In FIG. 2a, if the energy from the incident light is at a level n$_o$, so that the applied energy level is n$_o$, then there may be one or more nonradiative step decays indicated at 32 of the energy absorbed by the rare earth ions to a level 34, each step decay representing a phonon because, since it is a nonradiative decay, it is transformed into vibratory elastic energy in the crystal structure of the crystal. There may follow a radiative decay indicated by the abrupt change in energy level as indicated by the arrow 36 to a level 38 and then there may follow one or more nonradiative decays indicated by the levels 40, again indicating a transfer by phonons of energy until the lowest energy level 42 above the so-called ground level 44 is reached.

A similar situation may occur in accordance with the diagram of FIG. 2b, indicating that the radiation of light 14 is absorbed at an energy level n$_o$ again resulting in a multiphonon decay 46 and thereafter a radiative decay 48 to the lowest level 42.

FIG. 2c illustrates still another situation in which the absorbed energy of the radiation 14 at level n$_o$ decays by one or more radiative decays 56, 52 directly to the lowest level 42. In the case of FIG. 2c, there is no phonon energy and the crystal is not excited by any vibratory elastic energy.

The diagrams of FIG. 2a, 2b and 2c, are not intended to show every possible situation completely, but merely to indicate the nature of the energy transfer from the light 14 to the rare earth ions which absorb it and then return to their original energy levels from the excited state by radiation or by phonons or by combination of radiation or phonons.

The operation of the system can be explained in a qualitative manner and also in a more rigorous scientific manner. In this portion of the specification, we will adopt the former explanation and then follow it with the latter explanation which involves some mathematics. Let the matrix for the rare earth ions be exemplified by a transparent bar or rod 16 as illustrated in FIG. 1. The dimensions of the rod 16 are chosen in such a way that the rod is susceptible to its lowest resonant frequency well separated from the nearest higher frequency of resonance. The laser 10 is modulated by the modulator 12 at this resonant frequency, which is the mechanical resonant frequency of the rod 16.

On reception of energy from the laser 10, the rare earth ions will absorb some of the energy, especially if the radiant energy 14 is chosen to be at or near a particularly absorbent energy level for the rare earth ions. If the energy is reradiated as light, the bar 16 is not otherwise affected. Nevertheless, if the absorbed energy is given up in part as phonon energy, it will be apparent that the bar is subjected to a vibratory elastic energy at a modulation rate equal to the modulation frequency of the modulator 12. Because the rod or bar 16 has a high Q, the vibratory energy is transformed into mechanical oscillatory energy of the bar in effect by an action which may be explained as comparable to parametric oscillations. The mechanical oscillations of the bar in such a way will be multiplied by the mechanical Q of the bar, which may be very great, so that the system will be very sensitive to energy levels whose decay is by phonons and insensitive to energy levels that decay radiatively.

The laser source 10 may be tunable and therefore may serve as a highly sensitive tool to examine the method of and decay of the excited state of the rare earth ions in the crystalline matrix 16. Similarly, this provides a tool to examine the line width mechanisms of the ions. The phonon assisted energy transfer processes themselves may be thus examined. The system and method therefore affords a way of investigating many important questions.

The Q of the system may be further enhanced by resort to operation in a cyrogenic medium or atmosphere, if desired.

In preparing the bar which is a solid containing the rare earth ions to be resonant at a selected frequency $w_o$, $$W_o = 2\pi f_o \tag{1}$$

the amplitude modulation frequency. This frequency should lie in the region:

$$\tfrac{1}{4}c/L \leq f_o \leq \tfrac{1}{2}c/L \tag{2}$$

where L is the length of the solid and c is the speed of sound in the bar. For a simple bar $$c = \sqrt{r/q} \tag{3}$$

where r is Young's modulus and q is the density of the bar 16.

For glass (pyrex), c is approximately 5,200 meters/second, and for quartz c is about 5,450 meters/second. For a rod or bar of about 1/10 cm. in length, the resultant frequency is a few kilocycles for the lowest mode of the bar. This will be the selected frequency at which the incoming laser beam will be modulated. The bar may be attached to the piezoelectric transducer 20 in known fashion, and if desired may be calibrated after attachment so that the frequency can be known extremely accurately. The bar also is preferably shaped so that no modes of mechanical oscillation are near, that is, the length of the bar is much greater (let us say 10 times greater) than any of the other dimensions. A system of this kind may have a very high Q factor. For example, quartz in air can have a Q factor of as high as 27,500, while in vacuum the Q of such a bar may be as high as $10^6$. Even though the bar is somewhat loaded by its attachment to the piezoelectric crystal, it is still an extremely high Q system.

The electric vector in the incident light can be written as:

$$E_z = E_0 \cos wt [1 + \delta m \cos \omega_m t] \tag{4}$$

where $\delta_m$ is the modulation amplitude and where $\omega_m$ is the modulating frequency. Also $$w = 2\pi/\lambda \tag{5}$$

where $\lambda$ is the wavelength of the incident light 14.

The wave $E_z$ (where $E_z$ denotes the field strength in the direction z of the incident radiation) can then be written as:

$$E_z = E_o \cos wt + \frac{E_o \delta m}{2}[\cos(w + w_m)t + \cos(w - w_m)t] \tag{6}$$

Then the wave at point X distant from the free end of the bar may be written as $$E_z \text{ at } x = \Sigma A\mu \cos(k\mu x - w\mu t)$$

$$\mu = -1, 0, +1 \tag{7}$$

in which $k\mu = w\mu/c$, $w\mu = w + \mu w_m$, $A_o = E_o$, and $A_{\pm 1} = (E_o \delta m)/2$.

Now the intensity of the laser radiation 14 falling on the crystal bar 16 is proportional to the vector product $E \times H$, so the intensity I may be written as a proportionality:

$$I \sim \Sigma A\mu A\mu' \cos(k\mu x - w\mu t) \cos(k\mu' x - w\mu' t)\, \mu,\mu' \tag{8}$$

in which the subscript $\mu'$ denotes a value arising from H. So by trigonometric identity:

$$I \sim \Sigma A\mu A\mu' \tfrac{1}{2}\{\cos[(k\mu + k\mu')x - (w\mu + w\mu')t] + \cos[(k\mu - k\mu')x - (w\mu - w\mu')t]\} \tag{9}$$

The frequency of the first term in brackets, is much greater than the frequency of the second term in brackets, in equation 9. Therefore, we may assume that the higher frequency may be filtered out by any suitable known means, and we may consider the remaining lower frequency component, so that, at low frequencies, I becomes $I_{LF}$, and $$I_{LF} \sim \Sigma \frac{A\mu A\mu'}{2} \cdot \cos[(k\mu - k\mu')x - (w\mu - w\mu')t] \tag{10}$$

The various terms then arise from $\mu = \mu'$, which gives a constant, and the parings: $\mu = 1$, $\mu' = 0$, $\mu = 0$, $\mu = \pm 1$, $\mu = -1$, $\mu' =$ which gives $w_m$, as follows:

$$I_{LF} = \Sigma \frac{A\mu^2}{2} + \sum_{\mu = \mu \pm 1} \frac{A\mu A\mu \pm 1}{2} \cos[(k\mu - k\mu \pm 1)x - (w\mu - w\mu \pm 1)t] + \sum_{\mu,\mu' = \mu \pm 2} \cdots \tag{11}$$

The remaining terms may be ignored because they will be insignificant in view of the nature of the summation and because of the system resonance and filtering.

Then the low frequency intensity becomes $$I_{LF} = A_o + A_1 \cos(k_m x - w_m t) \tag{12}$$

where $A_1$ and $A_2$ are constants and $k_m = 2\pi/\lambda_m$ which desirably assume values of a few hundred kilocycles. We may allow $k_m = 0$, nearly. Then $$I_{LF} = A_o + A_1 \cos w_m t \tag{13}$$

The number of rare earth atoms (or rare earth ions) 18 in the bar 16 in the excited states as a result of the radiation 14 is proportional to the intensity of the radiation 14. The number of phonons $n_p$ generated by a non-radiative decay is, in turn, proportional to the intensity. Therefore $$n_p = K[A_o + A_1 \cos w_m t] \tag{14}$$

where K is some constant. Then the number of time-dependent phonons generated is $$n_p(t) = KA_1 \cos w_m t \qquad (15)$$

This term (15) enters as a source term into the wave equation for the mechanical oscillation of the bar 16, which is the sample, driving the bar to oscillate at frequency $w_m$. If the bar is resonant at frequency $w_m$, as is supposed, the amplitude of the oscillation KA, will be multiplied by the Q of the mounted bar, which is very large as noted hereinbefore. Thus, the system is highly sensitive to the non-radiative energy level decay by phonons, and insensitive to energy levels that decay radiatively by photons. As noted above, the Q may be enhanced by operation in a cryogenic atmosphere or medium.

If the laser source is tunable, as indicated by arrow 54, being for example, a dye laser, then a sensitive tool is provided to examine the method of decay of the excited states of rare earth ions in crystals, and for examining the line-width mechanisms of such ions. Phonon-assisted energy processes can also be studied.

The system here described is useful in the investigation of the rare earth absorption and emission spectra in a single crystal. Many of the absorption lines of the rare earth ions in solids are very sharp, e.g. approximately 1 cm.$^{-1}$ half-width at 20,000 cm$^{-1}$. It is believed by some that much of this line width is caused by inhomogeneous regions in the sample, rather than by coupling of the ions to phonons. One prior way of investigating has been to test line widths as a function of temperature. The hypothesis is that if the line widths increase, these lines appear due to phonon activity; line widths that do not change with temperature may be considered due to the inhomogeneous regions. By employing both the present system and method and prior techniques the accuracy of this hypothesis may be ascertained. It is apparent from the foregoing that the present system and method provides a valuable tool for the study of phonons and phonon decay.

We claim:

1. In combination:
    a crystalline bar doped with a rare earth impurity having an absorption wavelength and mechanically resonant at a selected frequency and,
    a source of light received by said bar, the bar being transparent to the light, the light having a wavelength at said absorption wavelength, the light of said source being modulated at said selected resonance frequency.

2. In a combination as claimed in claim 1, said source comprising a laser.

3. In a combination as claimed in claim 2, further comprising a means for modulating the light from said laser.

4. In a combination as claimed in claim 3, said modulating means being a pulse modulator.

5. In a combination as claimed in claim 4, said crystalline bar being of LiYF$_4$ and said impurity being a rare earth.

6. In a combination as claimed in claim 1, the energy at said absorption wavelength exciting the rare earth impurity with which said bar is doped to provide the rare earth ions with excitation resulting in phonon decay of the excited states.

7. A method for indicating the excited state reactions of rare earth ions in a crystalline medium comprising the steps of:
    forming a mechanical bar of the crystalline medium doped with rare earth ions, said bar having a mechanically resonant frequency,
    exciting the bar with radiant energy near the excitation frequency of the ions in the bar and modulating said energy at the said mechanically resonant frequency, thereby to excite the rare-earth ions to provide non-radiative phonons which mechanically excite the bar at the said modulation frequency and thereby cause the bar to mechanically resonate,
    piezoelectrically transferring a portion of the resonant energy to electrical energy, and
    indicating the electrical energy thus transferred,
    thereby providing indication of the excited state reactions of said ions.

8. A method for studying the excited state reactions of rare earth ions in a crystalline solid comprising the steps of:
    exposing to a modulated light a bar mechanically resonant at the modulation frequency, transparent at the light frequency, and doped with rare earth ions excited by the light energy and
    detecting the resultant mechanical resonations of the bar.

9. A method as claimed in claim 8, further comprising the steps of measuring the amplitude of the detected resonations.

* * * * *